US005693778A

United States Patent [19]

Kruh et al.

[11] Patent Number: 5,693,778

[45] Date of Patent: Dec. 2, 1997

[54] ARG A HUMAN GENE RELATED TO BUT DISTINCT FROM ABL PROTO-ONCOGENE

[75] Inventors: Gary D. Kruh, Washington, D.C.; Stuart A. Aaronson, Great Falls, Va.

[73] Assignee: The United States of America as represented by the Department of Health and Human Services, Washington, D.C.

[21] Appl. No.: 559,029

[22] Filed: Jul. 30, 1990

Related U.S. Application Data

[63] Continuation-in-part of Ser. No. 135,280, Dec. 21, 1987, abandoned.

[51] Int. Cl.[6] .............................. C07H 21/04; C12Q 1/68

[52] U.S. Cl. ............................ 536/23.5; 435/6; 536/23.2; 536/24.31

[58] Field of Search ............................... 536/23.5, 24.31, 536/23.2; 435/6; 530/806, 350

[56] References Cited

U.S. PATENT DOCUMENTS 4,599,305 7/1986 Witte et al. ................................. 435/7

OTHER PUBLICATIONS

Fainstein et al. (1989) Oncogene 4: 1477–1481.
Perego et al. (1991) Oncogene 6(10): 1899–1902.
Reddy et al. (1983) Proc. Natl. Acad. Sci. 80: 3623–3627.
Kruh et al. 1986. Science, 234:1545–1548.
Kruh et al. 1990. Proc. Natl. Acad. Sci. 87:5802–5806.

*Primary Examiner*—Robert A. Wax
*Assistant Examiner*—Lisa J. Hobbs
*Attorney, Agent, or Firm*—Susan S. Rucker

[57] ABSTRACT

The invention concerns the isolation and sequencing of a new gene, arg, related to the abl proto-oncogene. The gene gets transcripted to two mRNA's; which in turn form two proteins. Antibodies, oligonucleotide probes and assays of detecting the arg gene, its mRNA and its protein products are also objects of the invention.

7 Claims, 28 Drawing Sheets

```
        10         20         30         40         50         60         70
GAAAAGCAGA ATCTGTGAGT CGCCTGGAGG CAGCGCGGCG GCTGCCGTGA GGAGGCCGGG TGCGGAGCCG

        80         90        100        110        120        130        140
CCGGTGGCCC AGCCGCTCAG GGCCAGGGCC TGGGCTGGGA GGGAGAGACC GGAGCAGCGC CAGGAGCCCG

       150        160        170        180        190        200        210
AGGCCGGAGC CGAGGAGGAA TGTGACCAGG GGTCGGCGGG GGCGCGGGAG TACGCGAGAG CAGGGATGGG

       220        230        240        250        260        270        280
GCAGCAGGTG GGCCGCGTCG GGGAAGCTCC GGGGCTCCAG CAGCCTCAGC CCCGCGGGAT CCGGGGCAGC

       290        300        310        320        330        340        350
AGTGCAGCCA GGCCCTCCGG CCGCAGGCGG GACCCGGCGG GGCGCACCAC AGAGACCGGC TTCAATATCT

       360        370        380        390        400        410        420
TCACCCAGCA TGATCACTTT GCCAGCTGTG TGGAGGATGG ATTTGAGGGA GACAAGACTG GAGGCAGTAG

       430        440        450        460        470        480        490
TCCAGAAGCT TTGCATCGTC CCTATGGTTG TGATGTTGAA CCCCAGGCAC TAAATGAGGC TATCAGGTGG
```

FIG. 5A(i)

```
       500        510        520        530        540        550        560
AGCTCCAAGG AGAACTTGCT CGGAGCCACT GAGAGTGACC CTAATCTCTT CGTTGCACTT TATGATTTTG

       570        580        590        600        610        620        630
TAGCAAGTGG TGATAACACA CTCAGCATCA CTAAAGGTGA AAAGCTACGA GTCCTTGGTT ACAACCAGAA

       640        650        660        670        680        690        700
TGGTGAGTGG AGTGAAGTTC GCTCTAAGAA TGGGCAGGGC TGGGTGCCAA GCAACTACAT CACCCCAGTG

       710        720        730        740        750        760        770
AACAGCCTGG AAAAACACTC CTGGTACCAT GGACCTGTGT CACGCAGTGC AGCTGAGTAT CTGCTCAGCA

       780        790        800        810        820        830        840
GTCTAATCAA TGGCAGCTTC CTGGTGCGAG AAAGTGAGAG TAGCCCTGGG CAGCTGTCCA TCTCGCTCAG

       850        860        870        880        890        900        910
GTACGAGGGA CGTGTGTATC ACTACAGGAT CAATACCACT GCAGATGGCA AGGTGTATGT GACTGCTGAG

       920        930        940        950        960        970        980
AGCCGCTTCA GCACCTTGGC AGAGCTTGTA CACCATCACT CCACAGTGGC TGATGGGCTG GTGACAACAT
```

FIG. 5A(ii)

| | | | | | | |
|---|---|---|---|---|---|---|
| 990 | 1000 | 1010 | 1020 | 1030 | 1040 | 1050 |
| TACACTACCC | AGCACCCAAG | TGTAATAAGC | CTACAGTCTA | TGGTGTGTCC | CCCATCCACG | ACAAATGGGA |
| 1060 | 1070 | 1080 | 1090 | 1100 | 1110 | 1120 |
| AATGGAGCGA | ACAGATATTA | CCATGAAGCA | CAAACTTGGG | GGCGGTCAGT | ATGGAGAGGT | TTACGTTGGC |
| 1130 | 1140 | 1150 | 1160 | 1170 | 1180 | 1190 |
| GTCTGGAAGA | AATACAGCCT | TACAGTTGCT | GTGAAAACAT | TGAAGGAAGA | TACCATGGAG | GTAGAAGAAT |
| 1200 | 1210 | 1220 | 1230 | 1240 | 1250 | 1260 |
| TCCTGAAAGA | AGCTGCAGTA | ATGAAGGAAA | TCAAGCATCC | TAATCTGGTA | CAACTTTTAG | GTGTGTGTAC |
| 1270 | 1280 | 1290 | 1300 | 1310 | 1320 | 1330 |
| TTTGGAGCCA | CCATTTTACA | TTGTGACTGA | ATACATGCCA | TACGGGAATT | TGCTGGATTA | CCTCCGAGAA |
| 1340 | 1350 | 1360 | 1370 | 1380 | 1390 | 1400 |
| TGCAACCGAG | AAGAGGTGAC | TGCAGTTGTG | CTGCTCTACA | TGGCCACTCA | GATTTCTTCT | GCAATGGAGT |
| 1410 | 1420 | 1430 | 1440 | 1450 | 1460 | 1470 |
| ACTTAGAGAA | GAAGAATTTC | ATCCATAGAG | ATCTTGCAGC | TCGTAACTGC | CTAGTGGGAG | AAAACCATGT |

FIG. 5A(iii)

```
      1480       1490       1500       1510       1520       1530       1540
GGTAAAAGTG GCTGACTTTG GCTTAAGTAG ATTGATGACT GGAGACACTT ATACTGCTCA TGCTGGAGCC

      1550       1560       1570       1580       1590       1600       1610
AAATTTCCTA TTAAGTGGAC AGCACCAGAG AGTCTTGCCT ACAATACCTT CTCAATTAAA TCTGACGTCT

      1620       1630       1640       1650       1660       1670       1680
GGGCTTTTGG GGTATTGTTG TGGGAAATTG CTACCTATGG AATGTCACCA TATCCAGGTA TTGACCTGTC

      1690       1700       1710       1720       1730       1740       1750
TCAGGTCTAT GACCTACTAG AAAAAGGATA TCGAATGGAA CAGCCTGAGG GATGCCCCCC TAAGGTTTAT

      1760       1770       1780       1790       1800       1810       1820
GAACTTATGA GAGCATGCTG GAAGTGGAGC CCTGCCGATA GGCCCTCTTT TGCTGAAACA CACCAAGCTT

      1830       1840       1850       1860       1870       1880       1890
TTGAAACCAT GTTCCATGAC TCCAGCATTT CTGAAGAGGT AGCTGAGGAG CTTGGGAGAG CCGCCTCCTC

      1900       1910       1920       1930       1940       1950       1960
GTCATCTGTT GTTCCATACC TGCCCCGGCT ACCTATACTT CCTTCCAAGA CTCGGACACT GAAGAAACAG
```

FIG. 5A(iv)

```
      1970       1980       1990       2000       2010       2020       2030
GTGGAGAACA AGGAGAACAT TGAAGGGGCA CAAGATGCCA CAGAAAATTC TGCTTCCAGT TTAGCACCAG

      2040       2050       2060       2070       2080       2090       2100
GGTTCATCAG AGGTGCACAG GCCTCTAGTG GATCCCCAGC ACTGCCTCGA AAGCAAAGAG ACAAGTCACC

      2110       2120       2130       2140       2150       2160       2170
CAGCAGCCTC TTGGAAGATG CCAAAGAGAC ATGCTTCACC AGGGATAGGA AGGGGGGCTT CTTCAGCTCC

      2180       2190       2200       2210       2220       2230       2240
TTCATGAAGA AGAGAAATGC TCCTACACCC CCCAAACGCA GCAGCTCCTT CCGAGAAATG GAGAATCAGC

      2250       2260       2270       2280       2290       2300       2310
CCCATAAGAA ATACGAACTC ACGGGTAACT TCTCATCTGT TGCTTCTCTA CAGCATGCTG ATGGGTTCTC

      2320       2330       2340       2350       2360       2370       2380
TTTCACTCCT GCCCAGCAAG AGGCGAATCT GGTGCCACCC AAGTGCTATG GGGGGAGCTT TGCACAGAGG

      2390       2400       2410       2420       2430       2440       2450
AACCTCTGTA ATGACGACGG TGGTGGGGGT GGGGGCAGTG GCACTGCTGG GGGTGGGTGG TCTGGCATCA
```

FIG. 5A(v)

```
      2460       2470       2480       2490       2500       2510       2520
CAGGCTTCTT TACACCACGC TTAATCAAAA AGACACTGGG CTTACGAGCA GGTAAACCCA CAGCCAGTGA

      2530       2540       2550       2560       2570       2580       2590
TGACACTTCC AAGCCTTTTC CAAGGTCAAA CTCTACATCT TCCATGTCCT CAGGGCTTCC AGAGCAGGAT

      2600       2610       2620       2630       2640       2650       2660
AGGATGGCAA TGACCCTTCC CAGGAACTGC CAGAGGTCCA AACTCCAGCT GGAAAGGACA GTGTCCACCT

      2670       2680       2690       2700       2710       2720       2730
CTTCTCAGCC AGAAGAGAAT GTGGACAGGG CCAATGACAT GCTTCCAAAA AAATCAGAGG AAAGTGCTGC

      2740       2750       2760       2770       2780       2790       2800
TCCAAGCAGG GAGAGACCAA AAGCCAAGTT ATTGCCCAGA GGAGCCACAG CTCTTCCTCT CAGAACACCC

      2810       2820       2830       2840       2850       2860       2870
TCTGGGGATC TAGCCATTAC AGAGAAGGAC CCTCCAGGGG TGGGAGTGGC TGGAGTGGCA GCTGCCCCCA

      2880       2890       2900       2910       2920       2930       2940
AGGGTAAAGA GAAGAATGGT GGGGCACGAC TTGGGATGGC TGGAGTTCCA GAGGATGGAG AGCAGCCGGG
```

FIG. 5A(vi)

```
      2950       2960       2970       2980       2990       3000       3010
CTGGCCTTCT CCAGCCAAGG CTGCCCCCGT CCTCCCAACC ACTCACAACC ACAAAGTGCC AGTCCTTATC

      3020       3030       3040       3050       3060       3070       3080
TCACCCACTC TGAAACACAC TCCAGCTGAC GTGCAGCTCA TTGGCACAGA CTCTCAGGGG AATAAATTCA

      3090       3100       3110       3120       3130       3140       3150
AGCTCTTATC TGAGCATCAG GTCACATCCT CTGGAGACAA GGACCGACCC CGACGGGTAA AACCAAAGTG

      3160       3170       3180       3190       3200       3210       3220
TGCCCCACCC CCACCACCAG TGATGAGACT ACTGCAGCAT CCGTCCATCT GCTCAGACCC TACAGAAGAG

      3230       3240       3250       3260       3270       3280       3290
CCAACTGCCC TAACTGCAGG ACAGTCCACA TCAGAAACAC AGGAAGGAGG AAAGAAGGCA GCTCTGGGCG

      3300       3310       3320       3330       3340       3350       3360
CAGTGCCCAT CAGTGGGAAA GCTGGGAGGC CAGTGATGCC TCCACCTCAA GTGCCTCTGC CCACATCTTC

      3370       3380       3390       3400       3410       3420       3430
CATCTCGCCA GCCAAAATGG CCAATGGCAC AGCAGGTACT AAAGTGGCTC TGAGAAAAAC CAAACAGGCC
```

FIG. 5A(vii)

```
      3440       3450       3460       3470       3480       3490       3500
GCTGAGAAAA TCTCAGCAGA CAAAATCAGC AAAGAGGCCC TGCTGGAATG TGCTGACCTA CTGTCCAGTG

      3510       3520       3530       3540       3550       3560       3570
CACTCACGGA ACCTGTGCCC AACAGCCAGC TGGTAGACAC TGGACACCAG CTGCTTGACT ACTGCTCAGG

      3580       3590       3600       3610       3620       3630       3640
CTATGTGGAC TGCATCCCTC AAACTCGCAA CAAATTTGCC TTCCGAGAGG CTGTGAGCAA ACTGGAACTC

      3650       3660       3670       3680       3690       3700       3710
AGCCTGCAGG AGCTACAGGT TTCTTCAGCA GCTGCTGGTG TGCCCGGGAC AAACCCTGTC CTTAATAACT

      3720       3730       3740       3750       3760       3770       3780
TATTGTCATG TGTACAGGAA ATCAGTGATG TGGTGCAGAG GTAGCCACTG TTAGCCTGGT GGGAAAATGC

      3790       3800       3810       3820       3830       3840       3850
ACACATTTCT GAGGGGAGAG GGAAAAGGAC TTGTTTTCCT GTGTTCTTGT TTTCAGAAAA TGAAAGACTC

      3860       3870       3880       3890       3900       3910       3920
ATACTTGAGT GTGTTTATGT GAAGTACCTC AGATCCCTGA GTTCTCACGT TTACAGTTTC ATCTCAAAAA
```

FIG. 5A(viii)

```
      3930       3940       3950       3960       3970       3980       3990
TAAGAAGCAA ACCACATAAG TATAGGAGAG GTAAATTAAG TGGGGGCAAG GCAGTAGTGG ACAGGGTTGG

      4000       4010       4020       4030       4040       4050       4060
AAACTGCACT GGAAAATAGG GAACATGTGT ATGTCATAAG GAAGGCAATG CAGCCCATCC CTACCTGGAA

      4070       4080       4090       4100       4110       4120       4130
TGCTGGGAAG TGCTAGGCAG GGCTGCTCTC AGCAAGACTG CAGCAGCTGC ACCCAGACCT GGGGCTCTGG

      4140       4150       4160       4170       4180       4190       4200
TAGGTACTAA TGGTGATTAT GCTCCAATTT ACCTAATGAA TTTGGTGGGA CAGCAGAAAA GAAAGCCTGG

      4210       4220       4230       4240       4250       4260       4270
GAATGTACCA AGAGAAATTT TTGTTCAGGG CTGTTGGAAG TAGCTGTTAG CCTTGCTTCC ACAAGGCCAT

      4280       4290       4300       4310       4320       4330       4340
TGCTGCTGTA ATAAGAACTG CAAATCAGAG TGCTACAACA TAAAACTGGG AAATATGGCC CTATCTGAAT

      4350       4360       4370       4380       4390       4400       4410
GCCTCTGTCC TATTTTCCGC TGGTGTATCA GTTAGTGCAG GAAGTAAAGA ATGCTGGAAA GTTGAATCAG
```

FIG. 5A(ix)

```
      4420       4430       4440       4450       4460       4470       4480
AAATTGAAAA CCTTCTAAAA TCTTACACAG ATTAGCAGAA GTCACTTCTC CCAGTCTGGT ATATTATTTC

      4490       4500       4510       4520       4530       4540       4550
ATAATGGACC AGGATCGGCT TCCTGCCTGT TGGTGGCTAT CTGTAAACCA TAAGTACAGG GGTCTCCCTA
```

FIG. 5A(x)

| 10 | 20 | 30 | 40 | 50 | 60 | 70 |
|---|---|---|---|---|---|---|
| MVLGTVLLPP | NTYGRDQDTS | LCCLCTEASE | SALPDLTEAL | HRPYGCDVEP | QALNEAIRWS | SKENLLGATE |
| 80 | 90 | 100 | 110 | 120 | 130 | 140 |
| SDPNLFVALY | DFVASGDNTL | SITKGEKLRV | LGYNQNGEWS | EVRSKNGQGW | VPSNYITPVN | SLEKHSWYHG |
| 150 | 160 | 170 | 180 | 190 | 200 | 210 |
| PVSRSAAEYL | LSSLINGSFL | VRESESSPGQ | LSISLRYEGR | VYHYRINTTA | DGKVYVTAES | RFSTLAELVH |
| 220 | 230 | 240 | 250 | 260 | 270 | 280 |
| HHSTVADGLV | TTLHYPAPKC | NKPTVYGVSP | IHDKWEMERT | DITMKHKLGG | GQYGEVYVGV | WKKYSLTVAV |
| 290 | 300 | 310 | 320 | 330 | 340 | 350 |
| KTLKEDTMEV | EEFLKEAAVM | KEIKHPNLVQ | LLGVCTLEPP | FYIVTEYMPY | GNLLDYLREC | NREEVTAVVL |
| 360 | 370 | 380 | 390 | 400 | 410 | 420 |
| LYMATQISSA | MEYLEKKNFI | HRDLAARNCL | VGENHVVKVA | DFGLSRLMTG | DTYTAHAGAK | FPIKWTAPES |
| 430 | 440 | 450 | 460 | 470 | 480 | 490 |
| LAYNTFSIKS | DVWAFGVLLW | EIATYGMSPY | PGIDLSQVYD | LLEKGYRMEQ | PEGCPPKVYE | LMRACWKWSP |

FIG. 5B(i)

```
       500        510        520        530        540        550        560
ADRPSFAETH QAFETMFHDS SISEEVAEEL GRAASSSSVV PYLPRLPILP SKTRTLKKQV ENKENIEGAQ

       570        580        590        600        610        620        630
DATENSASSL APGFIRGAQA SSGSPALPRK QRDKSPSSLL EDAKETCFTR DRKGGFFSSF MKKRNAPTPP

       640        650        660        670        680        690        700
KRSSSFREME NQPHKKYELT GNFSSVASLQ HADGFSFTPA QQEANLVPPK CYGGSFAQRN LCNDDGGGGG

       710        720        730        740        750        760        770
GSGTAGGGWS GITGFFTPRL IKKTLGLRAG KPTASDDTSK PFPRSNSTSS MSSGLPEQDR MAMTLPRNCQ

       780        790        800        810        820        830        840
RSKLQLERTV STSSQPEENV DRANDMLPKK SEESAAPSRE RPKAKLLPRG ATALPLRTPS GDLAITEKDP

       850        860        870        880        890        900        910
PGVGVAGVAA APKGKEKNGG ARLGMAGVPE DGEQPGWPSP AKAAPVLPTT HNHKVPVLIS PTLKHTPADV

       920        930        940        950        960        970        980
QLIGTDSQGN KFKLLSEHQV TSSGDKDRPR RVKPKCAPPP PPVMRLLQHP SICSDPTEEP TALTAGQSTS
```

FIG. 5B(ii)

```
       990       1000       1010       1020       1030       1040       1050
ETQEGGKKAA LGAVPISGKA GRPVMPPPQV PLPTSSISPA KMANGTAGTK VALRKTKQAA EKISADKISK

      1060       1070       1080       1090       1100       1110       1120
EALLECADLL SSALTEPVPN SQLVDTGHQL LDYCSGYVDC IPQTRNKFAF REAVSKLELS LQELQVSSAA

      1130       1140
AGVPGTNPVL NNLLSCVQEI SDVVQR
```

FIG. 5B(iii)

```
        10         20         30         40         50         60         70
ATGGTCCTTG GGACAGTTCT CCTTCCACCT AATACTTATG GCAGAGATCA GGACACTTCA CTTTGCTGCC

        80         90        100        110        120        130        140
TGTGCACTGA GGCCTCAGAA TCTGCTCTAC CCGACTTAAC AGAAGCTTTG CATCGTCCCT ATGGTTGTGA

       150        160        170        180        190        200        210
TGTTGAACCC CAGGCACTAA ATGAGGCTAT CAGGTGGAGC TCCAAGGAGA ACTTGCTCGG AGCCACTGAG

       220        230        240        250        260        270        280
AGTGACCCTA ATCTCTTCGT TGCACTTTAT GATTTTGTAG CAAGTGGTGA TAACACACTC AGCATCACTA

       290        300        310        320        330        340        350
AAGGTGAAAA GCTACGAGTC CTTGGTTACA ACCAGAATGG TGAGTGGAGT GAAGTTCGCT CTAAGAATGG

       360        370        380        390        400        410        420
GCAGGGCTGG GTGCCAAGCA ACTACATCAC CCCAGTGAAC AGCCTGGAAA AACACTCCTG GTACCATGGA

       430        440        450        460        470        480        490
CCTGTGTCAC GCAGTGCAGC TGAGTATCTG CTCAGCAGTC TAATCAATGG CAGCTTCCTG GTGCGAGAAA
```

FIG. 5C(i)

```
       500        510        520        530        540        550        560
GTGAGAGTAG CCCTGGGCAG CTGTCCATCT CGCTCAGGTA CGAGGGACGT GTGTATCACT ACAGGATCAA

       570        580        590        600        610        620        630
TACCACTGCA GATGGCAAGG TGTATGTGAC TGCTGAGAGC CGCTTCAGCA CCTTGGCAGA GCTTGTACAC

       640        650        660        670        680        690        700
CATCACTCCA CAGTGGCTGA TGGGCTGGTG ACAACATTAC ACTACCCAGC ACCCAAGTGT AATAAGCCTA

       710        720        730        740        750        760        770
CAGTCTATGG TGTGTCCCCC ATCCACGACA AATGGGAAAT GGAGCGAACA GATATTACCA TGAAGCACAA

       780        790        800        810        820        830        840
ACTTGGGGGC GGTCAGTATG GAGAGGTTTA CGTTGGCGTC TGGAAGAAAT ACAGCCTTAC AGTTGCTGTG

       850        860        870        880        890        900        910
AAAACATTGA AGGAAGATAC CATGGAGGTA GAAGAATTCC TGAAAGAAGC TGCAGTAATG AAGGAAATCA

       920        930        940        950        960        970        980
AGCATCCTAA TCTGGTACAA CTTTTAGGTG TGTGTACTTT GGAGCCACCA TTTTACATTG TGACTGAATA
```

FIG. 5C(ii)

```
       990       1000       1010       1020       1030       1040       1050
CATGCCATAC GGGAATTTGC TGGATTACCT CCGAGAATGC AACCGAGAAG AGGTGACTGC AGTTGTGCTG

      1060       1070       1080       1090       1100       1110       1120
CTCTACATGG CCACTCAGAT TTCTTCTGCA ATGGAGTACT TAGAGAAGAA GAATTTCATC CATAGAGATC

      1130       1140       1150       1160       1170       1180       1190
TTGCAGCTCG TAACTGCCTA GTGGGAGAAA ACCATGTGGT AAAAGTGGCT GACTTTGGCT TAAGTAGATT

      1200       1210       1220       1230       1240       1250       1260
GATGACTGGA GACACTTATA CTGCTCATGC TGGAGCCAAA TTTCCTATTA AGTGGACAGC ACCAGAGAGT

      1270       1280       1290       1300       1310       1320       1330
CTTGCCTACA ATACCTTCTC AATTAAATCT GACGTCTGGG CTTTTGGGGT ATTGTTGTGG GAAATTGCTA

      1340       1350       1360       1370       1380       1390       1400
CCTATGGAAT GTCACCATAT CCAGGTATTG ACCTGTCTCA GGTCTATGAC CTACTAGAAA AAGGATATCG

      1410       1420       1430       1440       1450       1460       1470
AATGGAACAG CCTGAGGGAT GCCCCCCTAA GGTTTATGAA CTTATGAGAG CATGCTGGAA GTGGAGCCCT
```

FIG. 5C(iii)

```
      1480       1490       1500       1510       1520       1530       1540
GCCGATAGGC CCTCTTTTGC TGAAACACAC CAAGCTTTTG AAACCATGTT CCATGACTCC AGCATTTCTG

      1550       1560       1570       1580       1590       1600       1610
AAGAGGTAGC TGAGGAGCTT GGGAGAGCCG CCTCCTCGTC ATCTGTTGTT CCATACCTGC CCCGGCTACC

      1620       1630       1640       1650       1660       1670       1680
TATACTTCCT TCCAAGACTC GGACACTGAA GAAACAGGTG GAGAACAAGG AGAACATTGA AGGGGCACAA

      1690       1700       1710       1720       1730       1740       1750
GATGCCACAG AAAATTCTGC TTCCAGTTTA GCACCAGGGT TCATCAGAGG TGCACAGGCC TCTAGTGGAT

      1760       1770       1780       1790       1800       1810       1820
CCCCAGCACT GCCTCGAAAG CAAAGAGACA AGTCACCCAG CAGCCTCTTG GAAGATGCCA AAGAGACATG

      1830       1840       1850       1860       1870       1880       1890
CTTCACCAGG GATAGGAAGG GGGGCTTCTT CAGCTCCTTC ATGAAGAAGA GAAATGCTCC TACACCCCCC

      1900       1910       1920       1930       1940       1950       1960
AAACGCAGCA GCTCCTTCCG AGAAATGGAG AATCAGCCCC ATAAGAAATA CGAACTCACG GGTAACTTCT
```

FIG. 5C(iv)

```
      1970       1980       1990       2000       2010       2020       2030
CATCTGTTGC TTCTCTACAG CATGCTGATG GGTTCTCTTT CACTCCTGCC CAGCAAGAGG CGAATCTGGT

      2040       2050       2060       2070       2080       2090       2100
GCCACCCAAG TGCTATGGGG GGAGCTTTGC ACAGAGGAAC CTCTGTAATG ACGACGGTGG TGGGGGTGGG

      2110       2120       2130       2140       2150       2160       2170
GGCAGTGGCA CTGCTGGGGG TGGGTGGTCT GGCATCACAG GCTTCTTTAC ACCACGCTTA ATCAAAAAGA

      2180       2190       2200       2210       2220       2230       2240
CACTGGGCTT ACGAGCAGGT AAACCCACAG CCAGTGATGA CACTTCCAAG CCTTTTCCAA GGTCAAACTC

      2250       2260       2270       2280       2290       2300       2310
TACATCTTCC ATGTCCTCAG GGCTTCCAGA GCAGGATAGG ATGGCAATGA CCCTTCCCAG GAACTGCCAG

      2320       2330       2340       2350       2360       2370       2380
AGGTCCAAAC TCCAGCTGGA AAGGACAGTG TCCACCTCTT CTCAGCCAGA AGAGAATGTG GACAGGGCCA

      2390       2400       2410       2420       2430       2440       2450
ATGACATGCT TCCAAAAAAA TCAGAGGAAA GTGCTGCTCC AAGCAGGGAG AGACCAAAAG CCAAGTTATT
```

FIG. 5C(v)

```
      2460       2470       2480       2490       2500       2510       2520
GCCCAGAGGA GCCACAGCTC TTCCTCTCAG AACACCCTCT GGGGATCTAG CCATTACAGA GAAGGACCCT

      2530       2540       2550       2560       2570       2580       2590
CCAGGGGTGG GAGTGGCTGG AGTGGCAGCT GCCCCCAAGG GTAAAGAGAA GAATGGTGGG GCACGACTTG

      2600       2610       2620       2630       2640       2650       2660
GGATGGCTGG AGTTCCAGAG GATGGAGAGC AGCCGGGCTG GCCTTCTCCA GCCAAGGCTG CCCCCGTCCT

      2670       2680       2690       2700       2710       2720       2730
CCCAACCACT CACAACCACA AAGTGCCAGT CCTTATCTCA CCCACTCTGA AACACACTCC AGCTGACGTG

      2740       2750       2760       2770       2780       2790       2800
CAGCTCATTG GCACAGACTC TCAGGGGAAT AAATTCAAGC TCTTATCTGA GCATCAGGTC ACATCCTCTG

      2810       2820       2830       2840       2850       2860       2870
GAGACAAGGA CCGACCCCGA CGGGTAAAAC CAAAGTGTGC CCCACCCCCA CCACCAGTGA TGAGACTACT

      2880       2890       2900       2910       2920       2930       2940
GCAGCATCCG TCCATCTGCT CAGACCCTAC AGAAGAGCCA ACTGCCCTAA CTGCAGGACA GTCCACATCA
```

FIG. 5C(vi)

```
      2950       2960       2970       2980       2990       3000       3010
GAAACACAGG AAGGAGGAAA GAAGGCAGCT CTGGGCGCAG TGCCCATCAG TGGGAAAGCT GGGAGGCCAG

      3020       3030       3040       3050       3060       3070       3080
TGATGCCTCC ACCTCAAGTG CCTCTGCCCA CATCTTCCAT CTCGCCAGCC AAAATGGCCA ATGGCACAGC

      3090       3100       3110       3120       3130       3140       3150
AGGTACTAAA GTGGCTCTGA GAAAAACCAA ACAGGCCGCT GAGAAAATCT CAGCAGACAA AATCAGCAAA

      3160       3170       3180       3190       3200       3210       3220
GAGGCCCTGC TGGAATGTGC TGACCTACTG TCCAGTGCAC TCACGGAACC TGTGCCCAAC AGCCAGCTGG

      3230       3240       3250       3260       3270       3280       3290
TAGACACTGG ACACCAGCTG CTTGACTACT GCTCAGGCTA TGTGGACTGC ATCCCTCAAA CTCGCAACAA

      3300       3310       3320       3330       3340       3350       3360
ATTTGCCTTC CGAGAGGCTG TGAGCAAACT GGAACTCAGC CTGCAGGAGC TACAGGTTTC TTCAGCAGCT

      3370       3380       3390       3400       3410       3420       3430
GCTGGTGTGC CCGGGACAAA CCCTGTCCTT AATAACTTAT TGTCATGTGT ACAGGAAATC AGTGATGTGG

TGCAGAGG
```

FIG. 5C(vii)

| | | | | | | |
|---|---|---|---|---|---|---|
| 10 | 20 | 30 | 40 | 50 | 60 | 70 |
| MGQQVGRVGE | APGLQQPQPR | GIRGSSAARP | SGRRRDPAGR | TTETGFNIFT | QHDHFASCVE | DGFEGDKTGG |
| 80 | 90 | 100 | 110 | 120 | 130 | 140 |
| SSPEALHRPY | GCDVEPQALN | EAIRWSSKEN | LLGATESDPN | LFVALYDFVA | SGDNTLSITK | GEKLRVLGYN |
| 150 | 160 | 170 | 180 | 190 | 200 | 210 |
| QNGEWSEVRS | KNGQGWVPSN | YITPVNSLEK | HSWYHGPVSR | SAAEYLLSSL | INGSFLVRES | ESSPGQLSIS |
| 220 | 230 | 240 | 250 | 260 | 270 | 280 |
| LRYEGRVYHY | RINTTADGKV | YVTAESRFST | LAELVHHHST | VADGLVTTLH | YPAPKCNKPT | VYGVSPIHDK |
| 290 | 300 | 310 | 320 | 330 | 340 | 350 |
| WEMERTDITM | KHKLGGGQYG | EVYVGVWKKY | SLTVAVKTLK | EDTMEVEEFL | KEAAVMKEIK | HPNLVQLLGV |
| 360 | 370 | 380 | 390 | 400 | 410 | 420 |
| CTLEPPFYIV | TEYMPYGNLL | DYLRECNREE | VTAVVLLYMA | TQISSAMEYL | EKKNFIHRDL | AARNCLVGEN |
| 430 | 440 | 450 | 460 | 470 | 480 | 490 |
| HVVKVADFGL | SRLMTGDTYT | AHAGAKFPIK | WTAPESLAYN | TFSIKSDVWA | FGVLLWEIAT | YGMSPYPGID |

FIG. 5D(i)

```
       500        510        520        530        540        550        560
LSQVYDLLEK GYRMEQPEGC PPKVYELMRA CWKWSPADRP SFAETHQAFE TMFHDSSISE EVAEELGRAA

       570        580        590        600        610        620        630
SSSSVVPYLP RLPILPSKTR TLKKQVENKE NIEGAQDATE NSASSLAPGF IRGAQASSGS PALPRKQRDK

       640        650        660        670        680        690        700
SPSSLLEDAK ETCFTRDRKG GFFSSFMKKR NAPTPPKRSS SFREMENQPH KKYELTGNFS SVASLQHADG

       710        720        730        740        750        760        770
FSFTPAQQEA NLVPPKCYGG SFAQRNLCND DGGGGGGSGT AGGGWSGITG FFTPRLIKKT LGLRAGKPTA

       780        790        800        810        820        830        840
SDDTSKPFPR SNSTSSMSSG LPEQDRMAMT LPRNCQRSKL QLERTVSTSS QPEENVDRAN DMLPKKSEES

       850        860        870        880        890        900        910
AAPSRERPKA KLLPRGATAL PLRTPSGDLA ITEKDPPGVG VAGVAAAPKG KEKNGGARLG MAGVPEDGEQ

       920        930        940        950        960        970        980
PGWPSPAKAA PVLPTTHNHK VPVLISPTLK HTPADVQLIG TDSQGNKFKL LSEHQVTSSG DKDRPRRVKP
```

FIG. 5D(ii)

```
       990       1000       1010       1020       1030       1040       1050
KCAPPPPPVM RLLQHPSICS DPTEEPTALT AGQSTSETQE GGKKAALGAV PISGKAGRPV MPPPQVPLPT

      1060       1070       1080       1090       1100       1110       1120
SSISPAKMAN GTAGTKVALR KTKQAAEKIS ADKISKEALL ECADLLSSAL TEPVPNSQLV DTGHQLLDYC

      1130       1140       1150       1160       1170       1180
SGYVDCIPQT RNKFAFREAV SKLELSLQEL QVSSAAAGVP GTNPVLNNLL SCVQEISDVV QR
```

FIG. 5D(iii)

ARG A HUMAN GENE RELATED TO BUT DISTINCT FROM ABL PROTO-ONCOGENE

This application is a continuation-in-part application of Ser. No. 07/135,280, filed Dec. 21, 1987, which is incorporated by reference, now abandoned.

BACKGROUND OF THE INVENTION

1. Technical Field

The present invention is related to the isolation, cloning and characterization of a hitherto unidentified human gene. More particularly, the present invention is related to the identification and cloning of a novel human gene closely related to but distinct from the abl proto-oncogene and which is a member of the tyrosine kinase encoding family of genes. The new gene of the present invention is designated herein as the "arg" gene, which stands for "Abelson Related Gene".

2. State of the Art

A number of genes have been identified as retroviral oncogenes that are responsible for inducing tumors in vivo and transforming cells in vitro (Land et al., *Science*, 222, 771–778, 1983). Some of them apparently encode transforming proteins that share a kinase domain homologous to that of $pp60^{src}$, a tyrosine specific protein kinase. The cellular cognate, encoded by the c-src gene, also exhibits tyrosine-specific kinase activity. Of particular interest is the fact that tyrosine-specific kinases are also encoded by other genes for several receptors for epidermal growth factors, including the receptors for epidermal growth factor (EGF) (Cohen et al., *J.Biol. Chem.*, 225, 4834–4842, 1980), platelet-derived growth factor (PDGF) (Nishimura, et al., *Proc. Natl. Acad. Sci* USA, 79, 4303–4307, 1982), insulin (Kasuga et al., *Nature*, 298, 667–669, 1982), and insulin-like growth factor I (Rubin, et al., *Nature*, 305, 438–440, 1983). This implies a link between the action of the growth factor-receptor complex and the oncogene products with tyrosine-specific kinase activity. Cytoplasmic protein tyrosine kinases, such as c-src, c-fps/fes and c-abl have been more difficult to investigate because of the inability to trigger them with specific ligands, their role in signal transduction is indicated by the resemblance of their catalytic domains to those of growth factor receptors (Hanks et al., *Science*, 241, 42–52, 1988) and the transforming ability of their transduced counterparts in naturally occurring retroviruses (Bishop, J. M. & Varmus, H. "RNA Tumor Viruses, eds. Weiss, R., Teich, N., Varmus, H., & Coffin, J., Cold Spring Harbor Lab., Cold Spring Harbor, N.Y., Vol. 2, 249–356, 1985).

Genetic alterations affecting proto-oncogenes of the tyrosine kinase family may play a role in spontaneous tumor development. A specific translocation affecting the c-abl locus, for example, is associated with chronic myelogenous leukemia (de Klein, et al., *Nature*, 300, 765, 1982; Collins, et al., *Proc. Natl. Acad. Sci.*, USA, 80, 4813, 1983). c-abl is also the transduced homolog of the transforming genes of Abelson murine leukemia virus (Shields, et al., *Cell*, 18, 955, 1980; Srinivasan, et al., *Proc. Natl. Acad. Sci*, USA,78, 2077, 1981) and Hardy-Zuckerman 2 feline sarcoma virus (Besmer, et al., *Nature*, 303, 825, 1983), replication-defective retroviruses that cause aggressive lymphomas in mice and fibrosarcomas in cats, respectively. In each of these cases, the activated forms of c-abl have in common an elevated level of tyrosine kinase activity (Kanopka, et al., *Cell*, 37, 1035, 1984; Witte, et al., *Nature*, 283, 826, 1980). Several recent studies have also documented amplification or rearrangement of the gene for the EGF receptor in certain human tumors (Liberman, et al., *Nature*, 313, 144, 1985), or tumor cell lines (Ullrich, et al., *Nature*, 309, 418, 1984; Lin, et al., *Science*, 224, 843, 1984). However, a gene that is a new member of the tyrosine kinase family which is closely related to, but distinct from the abl proto-oncogene, has not heretofore been known.

SUMMARY OF THE INVENTION

It is an object of the present invention to provide a novel, cloned, human gene having the nucleotide sequences shown in FIGS. 5A and 5C and described more fully herein infra.

It is a further object of the invention to provide RNAs transcripted from the nucleotide sequences of FIGS. 5A and 5C, and polypeptides encoded by the sequences of FIGS. 5A and 5C. The amino acid sequences of the polypeptides are given in FIGS. 5B and 5D.

It is still another object of the invention to provide antibodies, polyclonal and monoclonal, that react with the polypeptides; and a diagnostic kit containing said antibodies for the detection of the polypeptides.

It is another object of the present invention to provide a complimentary DNA (cDNA) clone homologous to the messenger RNA (mRNA) encoded by the cloned gene, said cDNA clone being capable of expressing large amounts of corresponding protein in a heterologous vector system, such as bacteria, yeast, eukaryotes, and the like.

It is yet another object of the present invention to produce a transformed cell or organism capable of expressing said gene by incorporating said gene or a part thereof into the genome of said cell, vector or organism.

It is still a further object of the present invention to provide nucleic acid probes and reagent kits capable of detecting said arg gene or a product thereof.

FIG. 1 shows the physical site map of λ arg 1 and the inserts of plasmids parg 1 and parg 2. A, Apa I; B, Bam HI; Bg, Bgl II; R, Eco RI; S, Sac I. The sites were determined by electrophoretic analysis of the products of single and double digestions. Regions of λarg 1 homologous to the 1.7-kbp v-abl probe were identified by hybridization as described in FIG. 2. Two homologous regions (dark bars) were contained in the plasmid subclones. The nucleotide sequence and predicted amino acid sequence of the regions homologous to v-abl are shown. Possible processing sites at the borders of the putative exons are shown in boxes. The underlined nucleotides were obtained by analysis of the region 5' to the first Bgl II site. Nucleotide sequence was performed by the dideoxy chain termination method (F. Sanger, et al., *Proc. Natl. Acad. Sci.*, USA, 74:5463, 1977).

FIG. 2A shows the detection of abl and abl-related gene fragments in human placenta and K562 cells. DNA (20 ug) was cleaved with Eco RI, separated by electrophoresis in agarose gels, and transferred to nitrocellulose paper (E. M. Southern, *J. Mol. Biol.*, 98: 503, 1975). Hybridization to $^{32}P$-labeled probe (P. W. J. Rigby, et al., *J. Mol. Biol.*, 113:237, 1977) was conducted in a solution of 40% or 30% formamide, 0.75 M NaCl, and 0.075 M sodium citrate, at 42° C. (G. M. Wahl, et al., *Proc. Natl. Acad. Sci.*, USA, 76:3863 (1979). After hybridization, the blots were washed first in 0.3 M NaCl plus 0.03 M sodium citrate at room temperature, and then in 0.015 M NaCl, 0.0015 M sodium citrate at 50° C. Hybridization was detected by autoradiography. (A Hybridization of a v-abl probe to placenta (lanes 2 and 4) or K562 (lanes 1 and 3) DNA under stringent (40% formamide) (lanes 1 and 2) or relaxed (30% formamide) (lanes 3 and 4) conditions. The probe was a 0.75-kbp Sau I-Sau I fragment of v-abl encompassing nucleotides 2489 to 3238 of the provirus (J. Groffen, et al., *Nature* (London), 304:167, 1983). FIG. 2B shows hybridization to placenta DNA of v-abl (lanes 1 and 2) and arg probes (lanes 3 and 4) under stringent (lanes 1 and 3) or relaxed (lanes 2 and 4) conditions. The v-abl probe was 1.7-kbp Hinc II-Winc II fragment encompassing nucleotides 1867 to 3600 of the provirus. The arg probe was 0.52-kbp Eco RI-Apa I fragment of plasmid parg 1.

FIG. 3A shows a comparison of the predicted amino acid sequences of the 5' (upper) and 3' (lower) exons of arg with v-abl (E. P. Reddy, et al., *Proc. Natl. Acad. Sci.*, USA, 80:3623, 1983), human c-abl (J. Groffen, et al., *Nature* (London), 304:167, 1983), chick c-src (A. P. Czernilofsky, et al., *Nature* (London), 287:193, 1980), human epidermal growth factor receptor (HER) (A. Ullrich, et al., *Nature* (London) 309:418, 1984, and human insulin receptor (HIR) (A. Ullrich, et al., *Nature* (London), 313: 756, 1985). Black regions represent identical amino acids. Sequence information was not available for the c-abl region homologous to the 5' exon. The tyrosine residue autophosphorylated in v-src is indicated by an asterisk. Single-letter abbreviations for the amino acid residues are: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr. FIG. 3B shows the detection of messenger RNA derived from the arg gene. Polyadenylated RNA of a human glioblastoma cell line was separated by denaturing gel electrophoresis in formaldehyde (H. D. Lehrach, et el., *Biochemistry*, 16 4743, 1977) and transferred to nitrocellulose. Hybridization of the filter with the arg probe was performed as described in the legend to FIG. 2. Hybridization was detected by autoradiography.

FIG. 4A shows the distribution of autoradiographic silver grains on normal human chromosomes after in situ hybridization with arg probe. Human metaphases and prometaphases from methotrexate-synchronized normal peripheral lymphocyte cultures (M. E. Chandler, et al., *Cytogenet. Cell Genet.*, 22:352, 1978) were pretreated with ribonuclease and denatured in 70% formamide—2× SSC (standard saline citrate) at 70° C. The arg probe was labeled with all four $_3$H— nucleotides (Amersham, Arlington Heights, Ill.) to high specific activity ($3.7\times10^7$ cpm/g DNA). A hybridization solution containing 50% formamide, 5% dextran sulfate, 5 mM EDTA, 2× Denhardt's solution. 300 mM NaCl, 30 mM sodium citrate, single-stranded salmon sperm DNA (50 g/ml), 200 mM phosphate buffer (pH 6.4) and $5\times10^5$ cpm of the labeled probe was layered onto each slide (M. E. Harper, et al., *Chromosoma (Berl.)*, 87:431, 1981). The slides were covered with cover slips and incubated in a moist chamber at 42° C. for 20 hours. After hybridizations, slides were washed successively in 50% formamide/2× SSC and 2× SSC at 42° C. For autoradiography, the hybridized slides were coated with nuclear track emulsion NTB-2 (Kodak, Rochester, N.Y. diluted 1:1 with $H_2O$ and stored at 4° C. for 14 days. For G-banding the slides were treated with a solution of 0.03% trypsin/0.012% EDTA (Gibco, Grant Island, N.Y.) and stained with 0.25% Wright stain in 0.06 M phosphate buffer (1:3, pH 6.8) (N. C. Popescu, et al., *Cytogenet. Cell Genet.*, 39:73, 1985). Previously photographed chromosome spreads were relocated and a second photomicrograh exhibiting G-bands was taken. Silver grains observed 233 cells were plotted on a 400-band human ideogram (*ISCN: An international System for Human Cytogenetic Nomenclature-High Resolution Banding.* Birth defects: Original article series, XVII, No. 5, March of Dimes Defects Foundation, New York, 1981). FIG. 4B shows the distribution of autoradiographic silver grains on chromosome 1. FIG. 4C shows Southern hybridization of DNA isolated from nine subclones of a single human-mouse somatic cell hybrid. DNA (10 g) was digested with Eco RI, fractionated by 0.7% agarose gel electrophoresis, and transferred to a nylon membrane. Hybridization was a $^{32}$P-labeled arg probe was performed as described (O. W. McBride, et al., *Proc. Natl. Acad. Sci.*, USA, 83:130, 1986) at 42° C. in 50% formamide and 10% dextran sulfate. Hybridization was detected by autoradiography after washing the membrane at 55° C. in 0.015 M NaCl, 0.0015 M sodium citrate, and 0.2% SDS. A 9-kbp mouse fragment homologous to arg was not detected under these stringent hybridization conditions.

FIGS. 5A(*i*)–5A(*x*) show the nucleotide sequence of the A transcript of the arg gene and FIGS. 5B(*i*)–5B(*iii*) show the amino acid sequence of the A form of the protein encoded by the A transcript of the arg gene. FIGS. 5C(*i*)–5C(*vii*) show the nucleotide sequence of the B transcript of the arg gene and FIGS. 5D(*i*)–5D(*iii*) show the amino acid sequence of the B transcript of the protein encoded by the B form of the arg gene. The nucleotide sequence in FIGS. 5A(*i*)–5A(*x*) and 5B(*i*)–5B(*iii*) correspond to the mRNA that encode the protein products, as such they are complementary to the template strand of the arg gene.

FIG. 6 shows the physical map of overlapping arg cDNA clones. The bar represents the open reading frame. cDNA clones were identified in K562 (K3), M426 (M6 and M7), and monocyte (MN2) cDNA libraries. The positions of overlapping cDNA clones were established by restriction mapping.

DETAILED DESCRIPTION OF THE INVENTION

The above and other objects and advantages of the present invention are achieved by a cloned human gene transcript having the nucleotide sequences shown in FIGS. 5A and 5C.

Although any methods and materials similar or equivalent to those described herein can be used in the practice or testing of the present invention, the preferred methods and materials are now described. All publications mentioned hereinbefore and hereinafter are incorporated by reference. Unless defined otherwise, all technical or scientific terms used herein have the same meaning as commonly understood by one of ordinary skill in the art to which this invention belongs.

Identification Of The "arg" Gene

In order not to rely upon the fortuitous identification of tumor cells carrying amplified c-abl related sequences, an attempt was made to detect such sequences in normal human DNA by molecular hybridization with a v-abl probe under conditions of low stringency. The tyrosine kinase-encoding domain of v-abl was selected as the probe, since this region is well conserved among members of the tyrosine kinase gene family.

Figure 1:
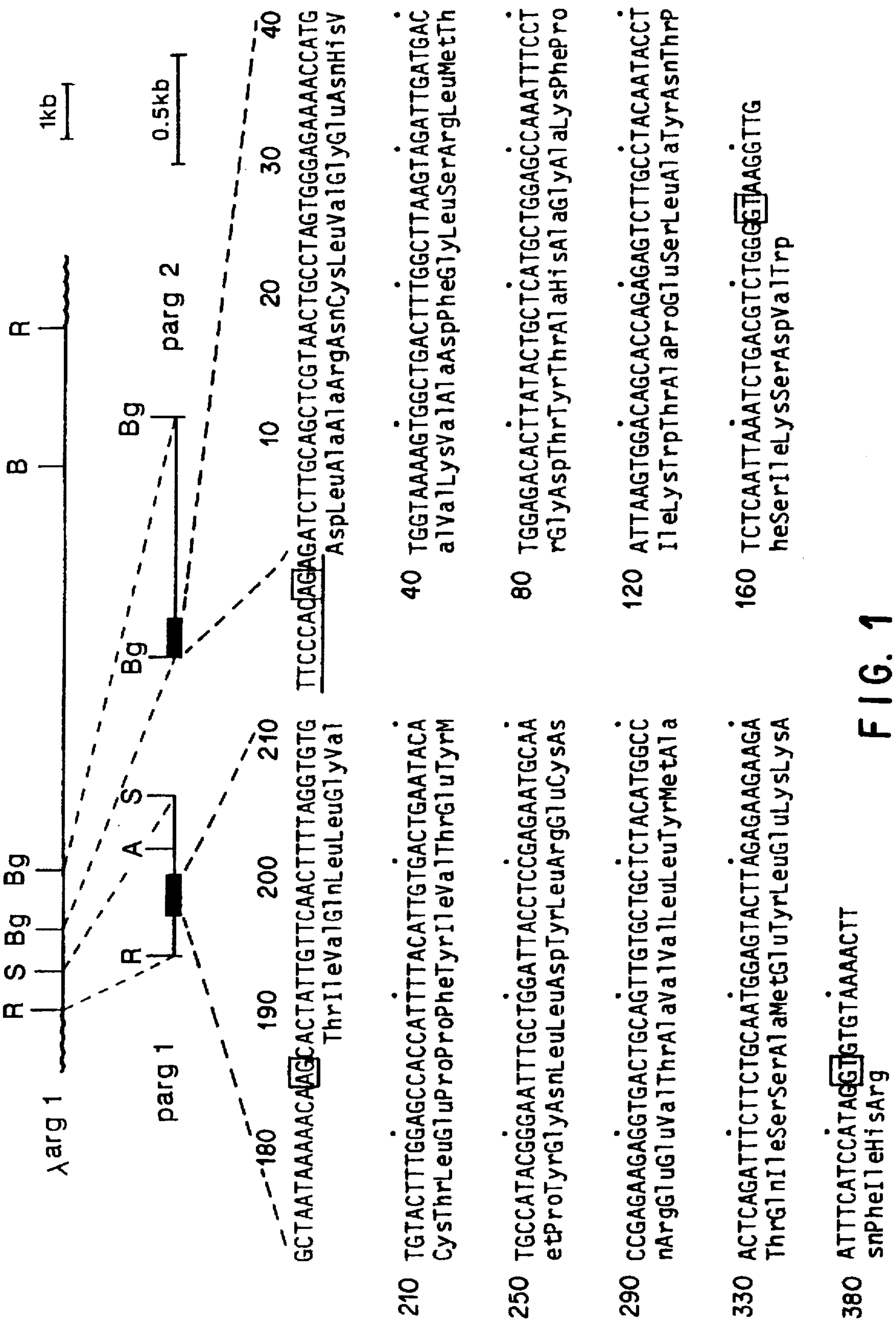
Figure 2A:
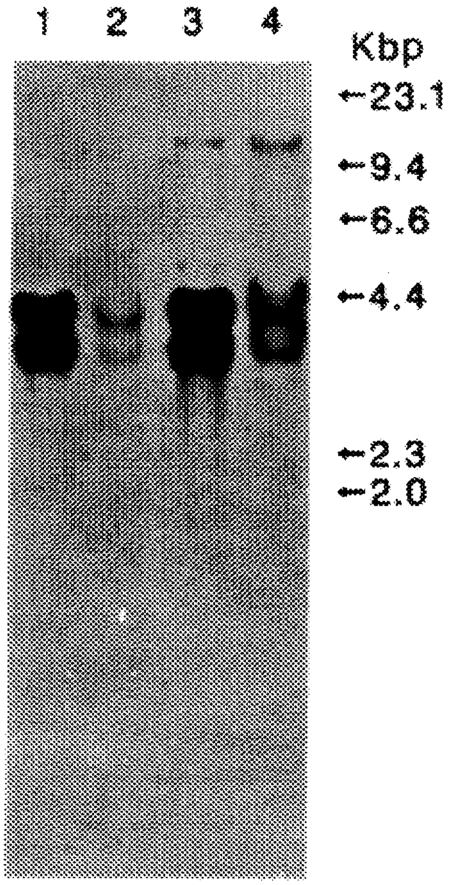

Hybridization of the v-abl probe under stringent conditions with DNA prepared from human placenta revealed two Eco RI fragments (FIG. 2A, lane 2) that contained c-abl sequences, as expected. However, when hybridization was conducted under conditions of low stringency, an additional 12.5-kbp fragment was identified (FIG. 2A, lane 4). This 12.5-kbp fragment was not amplified in DNA from K562 (FIG. 2A, lane 3), a CML line that contains an amplified copy number of c-abl, further suggesting that the additional fragment did not represent c-abl. To clone the 12.5-kbp fragment, an Eco RI digest of normal human placenta DNA was subjected to sucrose gradient centrifugation and a fraction containing fragments of about 12-kbp was ligated into lambda EMBL following standard techniques. The resulting bacteriophage library was screened by plaque hybridization under conditions of low stringency with a radiolabeled v-abl probe. The physical map of a hybridizing phage (lambda arg 1) containing a 12.5-kbp insert, and two pu18 subclones containing a 0.75-kbp Eco RI-Sac I fragment and a 1.1-kbp Bgl II-Bgl II fragment (parg 1 and parg 2, respectively) are shown in FIG. 1. Regions of the 12.5-kbp fragment homologous to v-abl were identified by hybridization of radioactive v-abl probe to Southern blots containing the products of restriction enzyme digestions. The subclones shown in FIG. 1 each contained one hybridizing fragment.

Figure 2B:
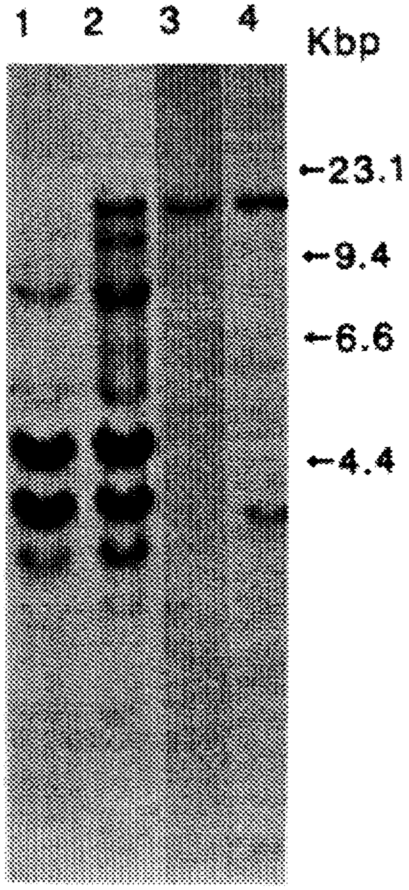

A single-copy DNA probe containing sequences homologous to v-abl was generated by digestion of parg 1 with Apa I and Eco RI. The specificity of this probe was demonstrated by hybridization with human placenta DNA digested with Eco RI. As expected, the 12.5-kbp fragment was detected under conditions of high stringency (FIG. 2B, lane 3), whereas an additional fragment containing c-abl sequence hybridized only under conditions of low stringency (FIG. 2B, lane 4).

Figure 6:
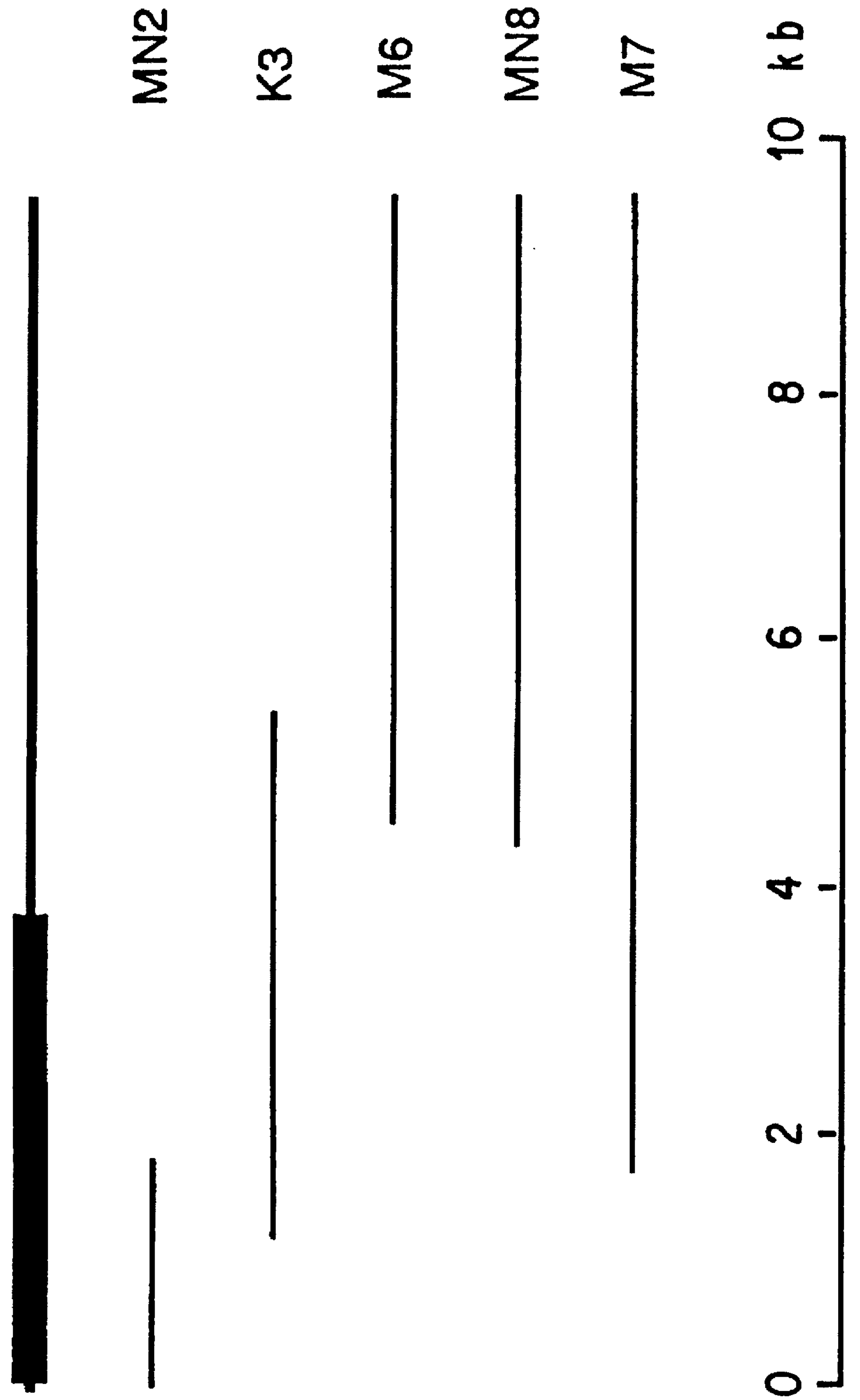

Initial arg cDNA clones were identified in a phage library prepared from K562 cells by using the arg probes described above. The longest arg cDNA clone derived from this library, K3, was used as a source of probes to isolate additional cDNA clones. Overlapping cDNA clones extending 5' and 3' of clone K3 could not be identified in the K562 library but were found in cDNA libraries prepared from M426 cells, monocytes and A172 cells. The overlapping arg cDNA clones, which together spanned 9.4 kb, are shown in FIG. 6. The cDNA libraries from the M426 and A172 cells were prepared as described in Miki et al., *Gene*, 83, 137 1989. The cDNA library from the K562 cells was prepared as in Mes-Masson et al., *Proc. Natl. Acad. Sci.*, USA 83, 9768–9772, 1986. The monocyte cDNA library was prepared by the same method as in the Miki et al., reference above, except monocytes were the source of the mRNA.

Nucleotide sequence analysis of arg cDNA revealed a long open reading frame of 3546 base pairs, extending from nucleotide 205–3750 in the cDNA. The open reading frame encoded a predicted protein of 1182 amino acids and was preceded by a 5' untranslated region high in G+C content. The location of the coding sequence at the 5' end of the cDNA leaves at least 6 kb of 3' untranslated sequence. Nucleotide sequence analysis of cDNA clones M6, M7 and MN8 revealed that their 3' sequences were identical but did not disclose a typical polyadenylation consensus motif. Thus it is possible that these three cDNA clones were generated by internal priming and that the additional sequence lies further downstream. It had been previously demonstrated by us that the arg gene is expressed as an approximately 12 kb transcript (G. D. Kruh *Science*,234, 1545–1548, 1986). It is also possible that additional non-coding sequence lies upstream of the arg coding region.

Analysis of the predicted arg protein product revealed features typical of members of the cytoplasmic tyrosine kinase family. A conserved tyrosine kinase domain spanned amino acids 281–532, and hydrophobic regions that could serve as signal peptide or transmembrane spanning domains were absent. A comparison among the arg protein product with the other known cytoplasmic tyrosine kinases, the c-abl, c-src and the c-fps gene products, reveals close similarities. In addition to conserved catalytic domains common to all tyrosine kinases, two conserved functional domains designated src homologous regions 2 and 3 (SH2 and SH3) have been identified in the c-abl and c-src proteins. An SH2 domain but not a SH3 domain has been identified in the c-fps protein. These domains are located amino-terminal to the kinase domains and appear to be involved in regulatory interactions. Comparison of the arg gene product with these three prototypic proteins showed that its structural architecture was strikingly similar to c-abl. arg and c-abl were readily distinguishable from the other cytoplasmic tyrosine kinases by virtue of their significantly larger sizes (1182 and 1148 amino acids, respectively) as well as the location of their catalytic domains amino-terminal to long carboxyl-terminal domains.

Comparison of the predicted amino acid sequences of arg and c-abl revealed a high degree of identity in their tyrosine kinase, SH2 and SH3 domains. Their tyrosine kinase domains were 94% identical, as compared with 52% and 44% for c-src and c-fes, respectively. The major tyrosine residue phosphorylated in vitro in c-abl was conserved in arg (arg position 439). The region in arg that extends amino-terminal from its catalytic domain to the position at which similarity with c-abl breaks (arg position 73) was 85% identical to c-abl. The latter region contains the arg SH2 and SH3 domains, each of which were 90% identical to those of c-abl.

The carboxyl-terminal domains of arg and c-abl, with 652 and 645 amino acids, respectively, were 29% identical. Although the overall similarity was weak, several conserved features were present. The greatest similarity in this domain was located at the extreme carboxyl terminus where the last 60 amino acids were 56% identical. A proposed nuclear localization sequence in murine c-abl consisting of five consecutive lysine residues was completely conserved in human c-abl and was represented by three consecutive basic amino acids in arg (lys-lys-arg). Several nuclear localization sequences consisting of three basic amino acids have been described, so it is possible that this sequence could be functional in arg. Two protein kinase C phosphorylation sites have been described in murine c-abl (Pendergast, et al., *Mol. Cell Biol.*, 7, 4280, 1987) and are completely conserved in the human protein. One of these sites, along with several residues immediately bordering it, was completely conserved in arg. The second site was only partially conserved and is unlikely to be functional since the serine residue that is apparently phosphorylated in c-abl was not present in the arg sequence. An unusual structural feature of c-abl is a proline rich (18%) region spanning amino acids 800–1000 (Shtivelman, et al., *Cell*, 47, 277, 1986). The analogous region of arg, spanning amino acids 848–1049, was also proline rich (16%). The location of these several conserved regions in a domain with otherwise poor similarity suggest important functions.

Nucleotide sequence analysis of several 5' arg clones revealed they could be classified into two types. The two classes of clones diverged from a common 3' sequence at precisely the same nucleotide and contained one of two types of upstream sequence. The sequences of both the transcripted nucleotides and the amino acids of the protein products are shown in FIG. 5. arg is expressed as two transcripts whose sizes are too similar to be allow them to be separated by agarose electrophoresis and encode proteins containing alternative amino termini. Human c-abl is also expressed as two transcripts of 6 and 7 kb that arise by a process of alternative splicing of 5' first exons (Shtivelman et al., supra). This generates two transcripts that diverge at their 5' ends but share a common 3' sequence and results in the synthesis of two proteins that differ only in their amino termini. A similar situation has also been described for murine c-abl. Genomic analysis has not been done with the arg gene to show that the arg splicing event involves first exons; however, by analogy with c-abl, the alternative 5' arg sequences have been designated A and B and it is assumed that they are joined to the arg second exon.

The arg gene appears to be a single-copy sequence since single hybridizing fragments were detected by Southern analysis of DNA separately digested with 11 restriction enzymes. Two fragments were found in DNA digested with PSt I, a restriction enzyme that has a site within an arg exon. No polymorphism was detected in DNA from 10 individuals with these 12 restriction endonucleases.

Figure 3A:
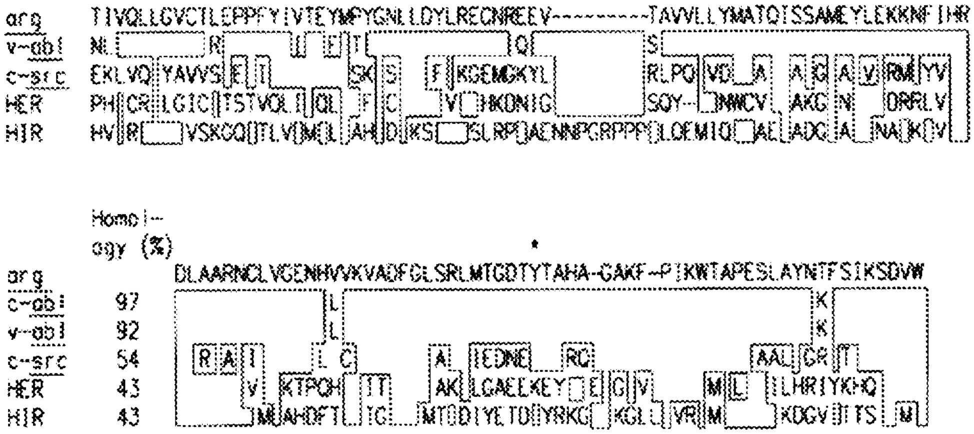
Figure 3B:
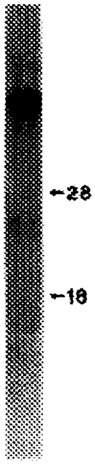

To establish that arg was a functional gene, its expression in polyadenylated RNAs of a variety of cells was investigated. A 12-kb transcript was readily detected by an arg probe in human brain tissue, fibroblasts, and several established tumor cell lines. A representative arg transcript (FIG. 3B) in a cell derived from a glioblastoma was distinct from the previously reported 6-kb and 7-kb c-abl transcripts (R. P. Gale, et al., *Proc. Natl. Acad. Sci.*, USA, 81, 5648, 1984). These findings demonstrate that arg is a new functional gene within the tyrosine kinase family.

Figure 4A:
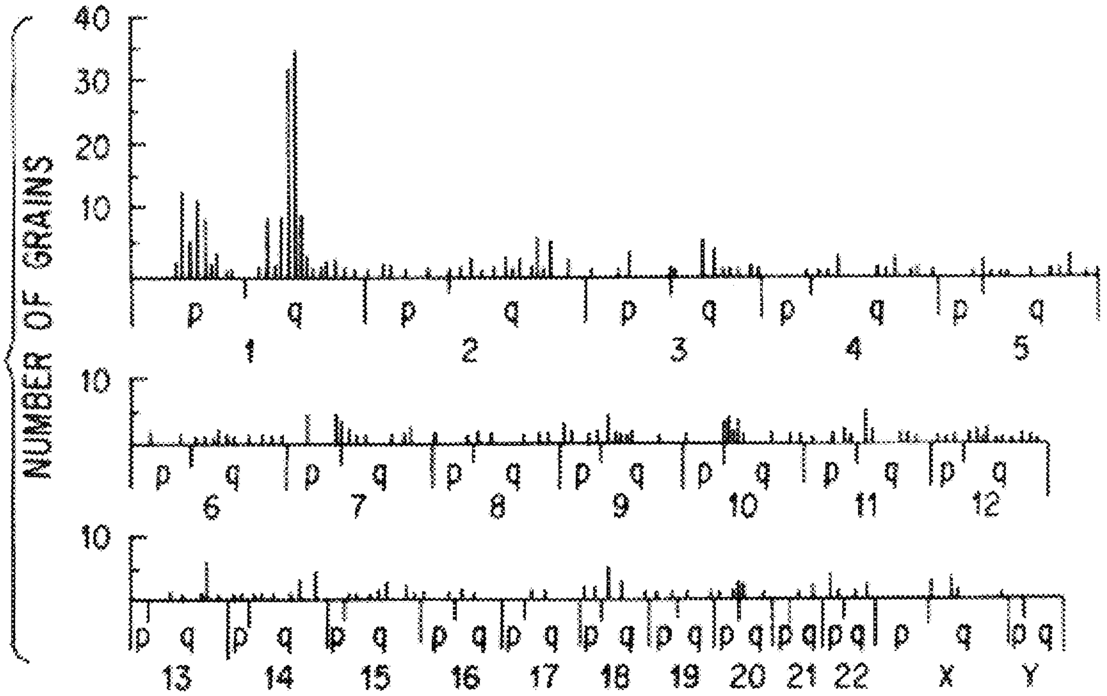
Figure 4B:
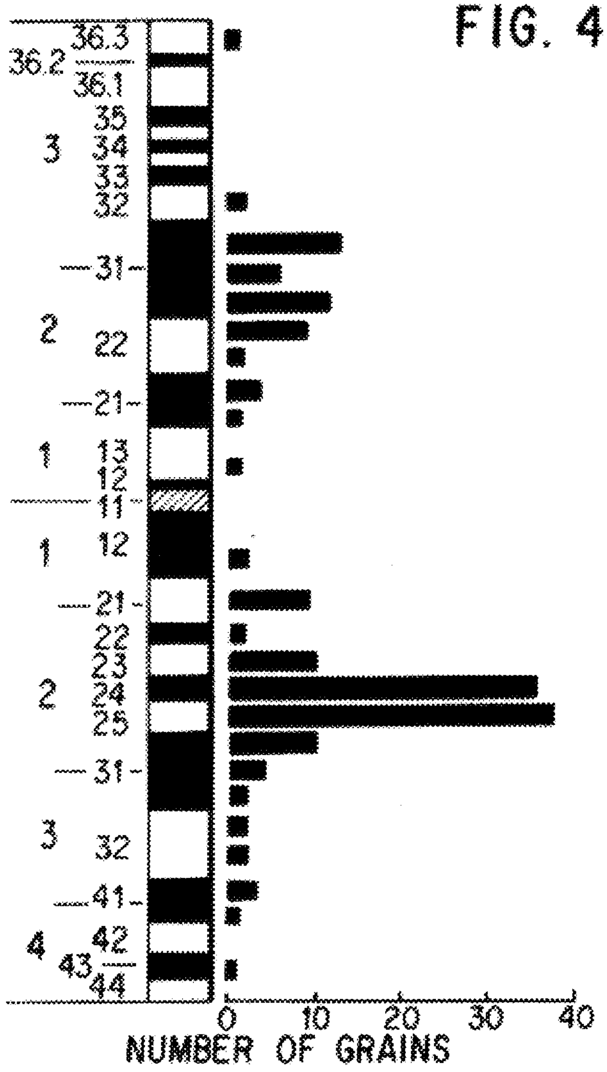

The chromosomal location of the human arg gene was determined by in situ hybridization on 233 chromosome spreads. About 169 grains (35% of total) was found on chromosome 1 (FIG. 4A). The largest number of grains (72) was on bands 1q24–25, which was equivalent to 43% of the grains on chromosome 1 and 15% of total grains scored (FIG. 4B). A minor site of hybridization on band 1p31 consisting of 31 grains accounted for 6% of the total number of grains. No other chromosome sites exhibited specific accumulation of grains.

As an independent approach to confirm the location of arg on the long arm of chromosome 1, 82 human-rodent somatic cell hybrids (O. W. McBride, et al., *J.Exp.Med.*, 155, 1480, 1982 and D. C. Swan, et al., *Proc. Natl. Acad. Sci.*, USA, 79, 4691, 1982) that segregate human chromosomes were analyzed. An arg probe detected as 12.5-kbp human Eco RI fragment specifically in DNA prepared from those hybrid cell lines that contained human chromosome 1. In contrast, there was at least 18% discordancy with all other human chromosomes.

Figure 4C:
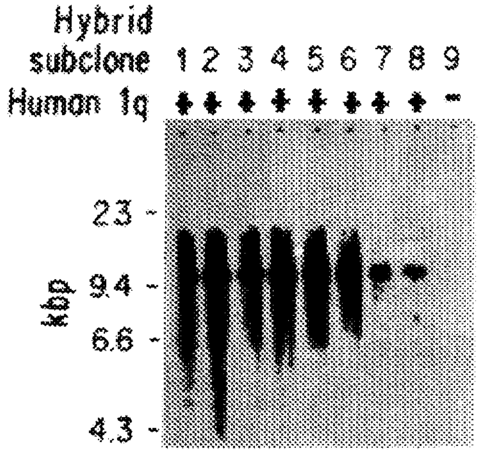

Analysis of hybrids containing segments of human chromosome 1 permitted regional localization of the arg gene on this chromosome. Among a series of nine subclones of a human-mouse hybrid cell line, eight retained an intact chromosome 1 and the arg sequence. One subclone, which contained a deletion of part of the long arm, lacked the arg gene (FIG. 4C). This subclone (lane 9) contained short arm markers including phosphoglucomutase-1, L-myc, N-ras, and the 6.2-kbp metallothionein sequence; whereas the 2.8-kbp metallothionein sequence and peptidase C long arm markers were not retained. An independent human-hamster hybrid was positive for human chromosome 1p isoenzyme markers 6-phosphogluconate dehydrogenase, phosphoglucomutase-1 and enolase-1; as well as the L-myc proto-oncogene (M. M. Nau, et al., *Nature*(London), 318, 69, 1985) and the 6.2-kbp metallothionein sequence (C. J. Schmidt, et al., *Science*,224, 1104, 1984). It lacked the human N-ras proto-oncogene located on proximal 1p as well as the 2.8-kbp metallothionein sequence and peptidase C on chromosome 1q. This hybrid, which lacked the long arm of chromosome 1 but retained most of the short arm, did not contain the arg gene. All of these results confirmed the assignment of arg to chromosome 1q by in situ hybridization and excluded a locus for this gone on the short arm of chromosome 1.

Generation of Nucleic Acid Probes

A nucleic acid probe is defined as a fragment of DNA or RNA whose nucleotide sequence (at least 8-bp, preferably 20-bp or larger) has at least partial identity with the sequence of the gene or its messenger RNA, such that the probe can hybridize to the gene or mRNA. Such probes allow the detection of the gene or its expression. Since a gene has potentially many fragments, there are a plurality of probes for detecting the gene. The probes are constructed by means known in the art. For the arg gene, probes may be constructed by cleaving the plasmid parg 1 with Eco RI and ApaI restriction enzymes. Probes may also be chemically synthesized to be identical or complement to fragments of the sequences in FIGS. 5A or 5C. These probes may be labeled with detectable labels by means well known in the art. Detectable labels may be chosen from radioactive isotopes, i.e., $^{31}P$, $^{131}I$ or $^{125}I$, or enzymes, i.e., horseradish peroxidase, or luminescent labels such as fluorescein.

Preparation of Antibodies Specific For The Protein Products Of The Gene

Knowing the nucleotide sequence of the two mRNA transcripts from the arg gene results immediately in the amino acid sequence of the two protein products, shown in FIGS. 5B and 5D. Antibodies, both polyclonal and monoclonal, can be raised that react with the proteins and allow their detection and quantitation. The raising of antibodies, both polyclonal and monoclonal, that react with an antigen or epitope, and their use in immunoassays to measure the antigen or epitope are conventional. The critical element is the antigen or epitope. For this invention the antigens are the proteins of FIGS. 5B and 5D, or immunogenic fragments of these proteins. Epitopes are portions or fragments of these proteins which are not immunogenic by themselves, but become so after being linked to a carrier, such as BSA or KHL. The antigens and epitopes needed to raise the antibodies are produced in two ways. Firstly, they can be chemically synthesized using standard peptide synthesis techniques, either manually or automatically using a peptide synthesis machine. Secondly, they can be produced by placing the gene for the protein into a heterologous expression system, such as bacteria, letting the bacteria produce the protein and then isolating the protein by methods well known in the art. The antibodies are then used in conventional assay methods, such as immunofluorescence or ELISA assays, to detect the presence or measure the amount of the proteins of FIGS. 5B and 5D in a biological sample.

A diagnostic test on human body sample, in accordance with the present invention, can be performed by one or more procedures as follows.

1. DNA is isolated from the sample by standard methods well known in the art. The DNA is then analyzed by established methods, such as Southern Blot hybridization using standard techniques similar to those used in the analysis shown herein. Gene-specific probes (of the type described above) are labeled and used to detect the gene. Abnormalities, such as gene amplification or gene rearrangement, may then be detected. In addition, abnormalities such as gene amplification might also be detected by polymerase chain reaction (PCR) methodology usinf PCR primers designed according to the arg sequence.

2. RNA is isolated from a tumor sample by standard methods. This RNA is analyzed by standard blot hybridization techniques. Gene-specific probes are made radioactive by standard techniques and used for detecting the two mRNA products of the arg gene. This allows the detection of expression of the arg gene. Abnormalities, such as overexpression or abnormal forms of the mRNA may be detected.

In addition, the amount of mRNA may be quantitated by spot hybridization procedures in which serial dilutions of RNA is fixed to a nitrocellulose filter and the mRNA of the arg gene detected by using a nucleic acid probe. The foregoing techniques are standard. These tests allow detection of mRNA overexpression or alteration of structure.

When the two protein products of the arg gene are to be analyzed one method is by the Western Blot. The proteins are separated according to molecular size, for example by gel electrophoresis, transferred to nitrocellulose membranes and the proteins are detected by reaction with specific antibodies. Such a test is able to detect alterations in the quantity of protein as well as abnormal protein forms. With such an approach protein levels of the arg gene can be detected in human body samples. By using two different antibodies, each of which reacts with the differing amino-terminal sequences of the A and B protein forms it is possible to detect or quantitate both proteins.

In addition, specific antibodies may be used in the analysis of histological sections. These techniques, which are well known for other antibody specificities, involve the thin sectioning of biopsied material from a potential tumor, followed by reaction with specific antibodies. The antibody-antigen reaction is then made visible by a variety of standard methods including labeling with fluorescently tagged or ferritin tagged second antisera and the like. Such detection systems allow the detection of the localized aberrant display of the protein product of the arg gene.

Knowledge of the arg gene described herein also makes possible a means of cancer treatment. If it is found that some cancers display abnormally high quantities of one or both gene products on their surface, such tumors can be treated with antibodies specific for the gene product(s) which has been conjugated to a toxic substance, such as radioactive markers, biological modifiers or toxins and the like. Another treatment modality involves the assumption of overexpression. In this approach, a specific natural product, even if unidentified, but which has high binding affinity for the protein product of the gene described here is used to target toxins to the tumor cells.

Diagnostic Kits For The Detection Of The Protein Products Of The "arg" Gene

Kits useful for the detection and/or quantitation of the protein products of the arg gene are now disclosed.

a) Kits designed to detect the proteins by immunoblotting: These kits preferably comprise containers containing (a) homogenization solution 950 mM Tris-HCl, pH 7.5, 1% sodium dodecyl sulfate and 0.1% beta-mercaptoethanol for the extraction of protein sample from biopsied material from putative tumors; (b) reagents for the preparation of immunoblots of the protein samples (acrylamide gels are prepoured and contain 7.5% acrylamide, 0.025% bid acrylamide, 0.38 M Tris-HCL, pH 8.8, 0.1% sodium dodecyl sulfate; the nitrocellulose sheets will be formed to the gel size; and transfer buffer 0.25 M Tris-glycine pH 8.8, sodium dodecyl sulfate; the nitrocellulose sheets will be formed to the gel size; and transfer buffer 0.25 M Tris-glycine pH 8.8, 305 methanol); (c) specific antibody reagents for the detection of the protein products of the "arg" gene (antisera directed against either or both protein products (since the proteins have a shared carboxyl terminal region but different amino-terminal regions, it is possible to raise an antibody that will react with both proteins, or two different antibodies that will react with only one of the protein products) and reaction buffer containing 0.1 M Tris-HCl pH 7.5, 5.0 M EDTA, 0.25% gelatin, 0.1% nonidet P-40); and (d) reagents and instructions for visualization and interpretation of antibody-antigen interaction. The reagents for visualization include labeled specific binding proteins that specifically bind to the antibodies. The specific binding proteins include antibodies and protein A. The labels are those conventionally used in immunoassays, radioactive isotopes (I-131, I-125 etc.), enzymes (horseradish peroxidase etc.) and fluorescent (such as fluorescein). While this kit includes components ordinarily found and well known in the art, the critical component is the gene products-specific antibodies.

(b) Kits designed for the detection of the protein product of the arg gene in tissue sections. Such kits include instructions for preparation of sections; instructions and standard reagents for the preparation of slides for microscopy; $H_2O_2$ for removal of endogenous peroxidase; instructions for incubation with antibodies specific for the protein product of the erbB-related gene described here in a buffer solution preferably containing phosphate buffered saline; and second antibodies for detection (these may be coupled to peroxidase, biotin, or ferriten); and instructions for visualization of detection complex. In addition the kits may include: reagents and instructions for the preparation of sections from biopsied putative tumor material; specific antibody reagents for the protein products of arg and instructions for their reaction with the tissue section; and reagents and instructions with the tissue section; and reagents and instructions for the detection of the protein-antibody interaction either by immunofluorescence, ferritin conjugated second antibodies or other standard methods well known in the art.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A purified DNA molecule having a nucleotide sequence identical to or complementary to that shown in FIG. 5A or FIG. 5C.

2. A purified RNA molecule having a nucleotide sequence which corresponds to the nucleotide sequence of the DNA molecule shown in FIG. 5A or FIG. 5C.

3. A purified oligonucleotide probe of 520 bases, from the Eco RI to the Apa I sites of parg 1, which has a sequence which is identical or complementary to the DNA of claim 1.

4. The oligonucleotide probe of claim 3, wherein said probe is labeled with a detectable label.

5. The oligonucleotide probe of claim 4, wherein said label is a radioactive moiety, a fluorescent moiety or an enzyme.

6. A nucleic acid hybridization assay to detect the arg gene or its mRNA transcript in a sample, said method comprising the following steps:

a) contacting said sample with an oligonucleotide probe of claim 3, under conditions such that a hybrid will form between any arg nucleic acid sequences or any said mRNA in said sample and said oligonucleotide probe;

b) detecting the presence of said hybrid whereby said detecting specifically is indicative of the arg gene or its mRNA transcript.

7. A purified polynucleotide which codes for the protein having the amino acid sequence shown in FIG. 5B or FIG. 5D.

* * * * *